US00PP31575P2

(12) United States Plant Patent
Lim

(10) Patent No.: US PP31,575 P2
(45) Date of Patent: Mar. 24, 2020

(54) MINIATURE MULTIFLORA ROSE PLANT NAMED 'ALTCAPTAIN'

(50) Latin Name: *Rosa hybrida*
Varietal Denomination: ALTcaptain

(71) Applicant: Altman Specialty Plants, Inc, Vista, CA (US)

(72) Inventor: Peter Lim, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,554

(22) Filed: Nov. 30, 2018

(51) Int. Cl.
*A01H 5/02* (2018.01)
*A01H 6/74* (2018.01)

(52) U.S. Cl.
USPC ..... Plt./116
CPC ..... *A01H 6/74* (2018.05)

(58) Field of Classification Search
USPC ..... Plt./102, 108, 116, 122, 141, 149, 150, Plt./151, 123
CPC ..... A01H 5/0222
See application file for complete search history.

*Primary Examiner* — Kent L Bell
(74) *Attorney, Agent, or Firm* — Cassandra Bright

(57) ABSTRACT

A new and distinct miniature multiflora Rose cultivar named 'ALTcaptain' is disclosed, characterized by distinctive fully double red-purple, magenta-red flowers with a peppery fragrance. Plants are vigorous and can be grown on their own roots. Plants are upright, flower continuously and exhibit good resistance to blackspot diseases. The new variety is a *Rosa*, normally produced as an outdoor garden or container plant.

1 Drawing Sheet

Latin name of the genus and species: *Rosa hybrida.*
Variety denomination: 'ALTcaptain'.

BACKGROUND OF THE INVENTION

The new *Rosa* cultivar is a product of a planned breeding program conducted by the inventor, Peter Ping Lim. The objective of the breeding program was to produce vigorous new garden rose varieties with continuous blooming for ornamental commercial applications. The cross resulting in this new variety was made during May of 2013.

The seed parent is the variety *Rosa* 'KORsailer', U.S. Plant Pat. No. 11,147. The pollen parent is the unpatented variety *Rosa* 'P9001R'. The new variety was selected in 2014 by the inventor in a group of seedlings resulting from the 2013 crossing, in a nursery in Vista, Calif.

Asexual reproduction of the new cultivar has been performed by vegetative cuttings. This was first performed at a research greenhouse in Vista, Calif. in June 2014 and has shown that the unique features of this cultivar are stable and reproduced true to type in more than 5 successive generations.

SUMMARY OF THE INVENTION

The cultivar 'ALTcaptain' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTcaptain' These characteristics in combination distinguish 'ALTcaptain' as a new and distinct *Rosa* cultivar:

1. Vigorous miniature shrub garden rose.
2. Double flower with many (90 to 120) petals.

3. Earlier blooming.
4. Continuous flowering.
5. Strong red-purple magenta-red flower color.
6. Dark glossy foliage resistant to black spot and powdery mildew disease.
7. Plants can be grown on their own roots; grafting is not required.

PARENT COMPARION

Plants of the new cultivar 'ALTcaptain' are similar to plants of the seed parent, in most horticultural characteristics, however, plants of the new cultivar 'ALTcaptain' differ in the following:

1. Flowers of the new cultivar are red-purple magenta-red, flowers of the seed parent are white.
2. Flowers of the new cultivar have less petals than flowers of the seed parent.

Plants of the new cultivar 'ALTcaptain' are similar to plants of the pollen parent in most horticultural characteristics, however, plants of the new cultivar 'ALTcaptain' differs in the following;

1. Flowers of the new variety are smaller than flowers of the pollen parent.

COMMERCIAL COMPARISON

Plants of the new cultivar 'ALTcaptain' can be compared to the commercial variety *Rosa* 'Flower Carpet Red', U.S. Plant Pat. No. 10,084. These varieties are similar in most horticultural characteristics, however 'ALTcaptain' differs in the following:

1. The new variety produces about 90 to 120 petals, this comparator produces about 15 petals
2. This comparator is a clustered floribunda, 'ALTcaptain' is a miniature multiflora.

3. This comparator has a later blooming flower cycle than 'ALTcaptain'.
4. Plants of this comparator are taller than 'ALTcaptain'.

Plants of the new cultivar 'ALTcaptain' can also be compared to the commercial variety *Rosa* 'MEIneble', U.S. Plant Pat. No. 7,116. These varieties are similar in most horticultural characteristics, however 'ALTcaptain' differs in the following:

1. The new variety produces about 90 to 120 petals, this comparator produces about 5 petals
2. This comparator is a clustered flowering shrub rose, 'ALTcaptain' is a miniature multiflora.
3. Flowers of this comparator have a white eye not found in 'ALTcaptain'.
4. Plants of this comparator are taller, wider and more open than 'ALTcaptain'.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTcaptain' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTcaptain'.

Market classification: Miniature multiflora rose.

PROPAGATION

Time to initiate roots: About 15 days at approximately 20° C.

Time to produce a rooted cutting: About 35 days at approximately 20° C.

PLANT

Age of plant described: Approximately 2 years.

Growth habit: Compact.

Container size: 2 gallon.

Height: 21 cm.

Plant spread: 30 cm.

Rootstock: Own root.

Growth rate: Moderate.

Branching characteristics: Sympodial branching.

Length of primary lateral branches: Average range 8 to 14 cm.

Diameter of lateral branches: Approximately 4 to 5 mm.

Quantity branches: 6 to 8 main branches, moderate lateral branches, 10 to 20 lateral branches per main branch.

Branches—young wood:

*Diameter*.—Approximately 3 mm.

*Texture*.—Glabrous, dense soft, short thorns.

*Approximately density/quantity of prickles*.—Moderate.

*Color*.—Near Yellow-Green 144C, flushed Greyed-Red 179B.

Branches—old wood:

*Diameter*.—Approximately 5 to 9 mm.

*Color*.—Near Yellow-Green 146A.

*Texture*.—Glabrous. Very oldest wood at soil line develops woody striations.

*Thorns*.—Approximately density/quantity of thorns: Moderate. Approximately 1 per linear cm. Color of thorns: Immature: Near Yellow-Green 151D, apex Greyed-Orange 166A. Mature: Near Greyed-Orange 165C, apex Greyed-Orange 166A. Shape: Narrow deltoid, very weakly hooked. Height: Average 8 mm. Diameter: Base near 5 mm. Tip near 2 mm.

FOLIAGE

Leaf:

*Arrangement*.—Alternate and compound.

*Quantity*.—Average 5 to 9 per main branch.

*Internode*.—Average range 5 to 25 mm.

*Average length*.—Approximately 9.5 cm.

*Average width*.—Approximately 6.5 cm.

Rachis:

*Average length*.—Approximately 3.3 cm.

*Average diameter*.—Approximately 0.2 cm.

*Color*.—Near Green 139A.

*Texture*.—Glabrous all surfaces.

Leaflet:

*Quantity*.—3 or 5 per leaf, most commonly 5.

*Average length*.—Approximately 3.5 cm.

*Average width*.—Approximately 2.2 cm.

*Shape of blade*.—Ovate.

*Apex*.—Acute.

*Base*.—Rounded.

*Margin*.—Serrate.

*Appearance of top surface*.—Very glossy.

*Appearance of bottom surface*.—Matte.

*Texture of top surface*.—Glabrous.

*Texture of bottom surface*.—Glabrous.

*Color*.—Young foliage upper side: Near Green 137C, margin Greyed-Purple 187B. Young foliage under side: Near Green 138B, margin Greyed-Purple 187B. Mature foliage upper side: Near Green 139A. Mature foliage under side: Near Green 137C.

*Venation*.—Type: Reticulate. Venation color upper side: Near Green 139D. Venation color under side: Near Green 139D.

Petiole:

*Average length*.—Approximately 2.5 cm.

*Average diameter*.—Approximately 2 mm.

*Color*.—Upper surface: Near Green 139A. Lower surface: Near Green 139A.

*Petiole wing*.—Typically 10 mm long and 2 mm wide. Apex acute. Upper surface colored near Green 137A, lower surface colored near Green 137B.

*Texture*.—Glabrous.

FLOWER

Natural flowering season: Spring until Autumn.

Inflorescence type and habit: Sprays of fully double rotate flowers. 3 to 5 flowers typically clustered together.

Rate of flower opening: Approximately 4 days from bud to fully opened flower.
Flower longevity on plant: 10 to 14 days, after fully opened.
Quantity of flowers: 20 to 30 fully opened flowers and buds.
Flower size:
*Diameter*.—Approximately 5.0 to 6.5 cm.
*Height*.—Approximately 2.0 cm.
Peduncle:
*Length*.—2.0 to 4.0 cm.
*Diameter*.—3 mm.
*Color*.—Near Green 138A.
*Texture*.—Prickly.
Petals:
*Petal arrangement*.—Multiple rotate, overlapping whorls.
*Petal quantity*.—90 to 120.
*Length*.—2.3 cm.
*Width*.—2.4 cm.
*Shape*.—Orbicular.
*Margin*.—Entire, slight downward curve.
*Apex*.—Rounded, sometimes single notch on outermost petals. Innermost petals mucronate.
*Base*.—Very broad attenuate.
*Texture*.—Glabrous all surfaces.
Color: Petals.
*When opening*.—Upper surface: A color between Red 53B and Red-Purple N66B. Very small basal blotch near White 155D. Lower surface: Near Red-Purple 67A. Small basal blotch near White 155D.
*Fully opened*.—Upper surface: Near Red-Purple N66A Small basal blotch near White 155D. Lower surface: Near Red-Purple N66B Small basal blotch near White 155D.
*Color changes when aging*.—Upper surface: Near Red-Purple 67A with flush of N74A. Small basal blotch near White 155D. Lower surface: Near Red-Purple 67A, uppermost section N74B. Small basal blotch near White 155D.
Bud:
*Shape*.—Ovate.
*Length*.—Approximately 3 cm.
*Diameter*.—Approximately 2 cm.
*Color*.—Near Red 53A.
Sepals:
*Quantity*.—5.
*Length*.—1.7 cm.
*Width*.—9 mm.
*Shape*.—Deltoid.
*Apex*.—Apiculate.
*Margin*.—Entire.
*Color*.—Interior Surface: Near Green 138B. Exterior Surface: Near Green 137C.
*Texture*.—Densely and minutely pubescent upper and lower surfaces.
Receptacle:
*Length*.—1.0 cm.
*Width*.—1.6 cm.
*Shape*.—Flattened dome.
*Color*.—Near Green 143B.
Fragrance: Typical sweet rose scent.

REPRODUCTIVE ORGANS

Stamens:
*Quantity*.—Average range 20 to 40.
*Filament length*.—Approximately 7 mm.
*Filament color*.—Near Yellow 2D.
Anthers:
*Length*.—2 mm.
*Shape*.—Narrow globular.
*Color*.—Near Green-Yellow 1B.
*Pollen*.—Color: Near Yellow 2C. Quantity: Scant or none.
Pistil: Malformed, interspersed among inner petals.
*Number*.—Approximately 10.
*Pistil length*.—Approximately 6 mm.
*Style*.—Length: Approximately 4 mm. Color: Near Yellow 2D.
*Stigma*.—Shape: Linear. Color: Near Yellow 2D.
*Ovary color*.—Near Yellow 2D.
*Ovary shape*.—Irregular round or flattened.
*Ovary length*.—Average 2 to 3 mm.
*Ovary diameter*.—Average 2 to 3 mm.

OTHER CHARACTERISTICS

Seeds and fruits: Not observed.
Disease/pest resistance: Good overall disease resistance to normal pests and diseases typical of garden roses. Very good resistance to blackspot diseases.

What is claimed is:

1. A new and distinct miniature multiflora Rose plant named 'ALTcaptain' as herein illustrated and described.

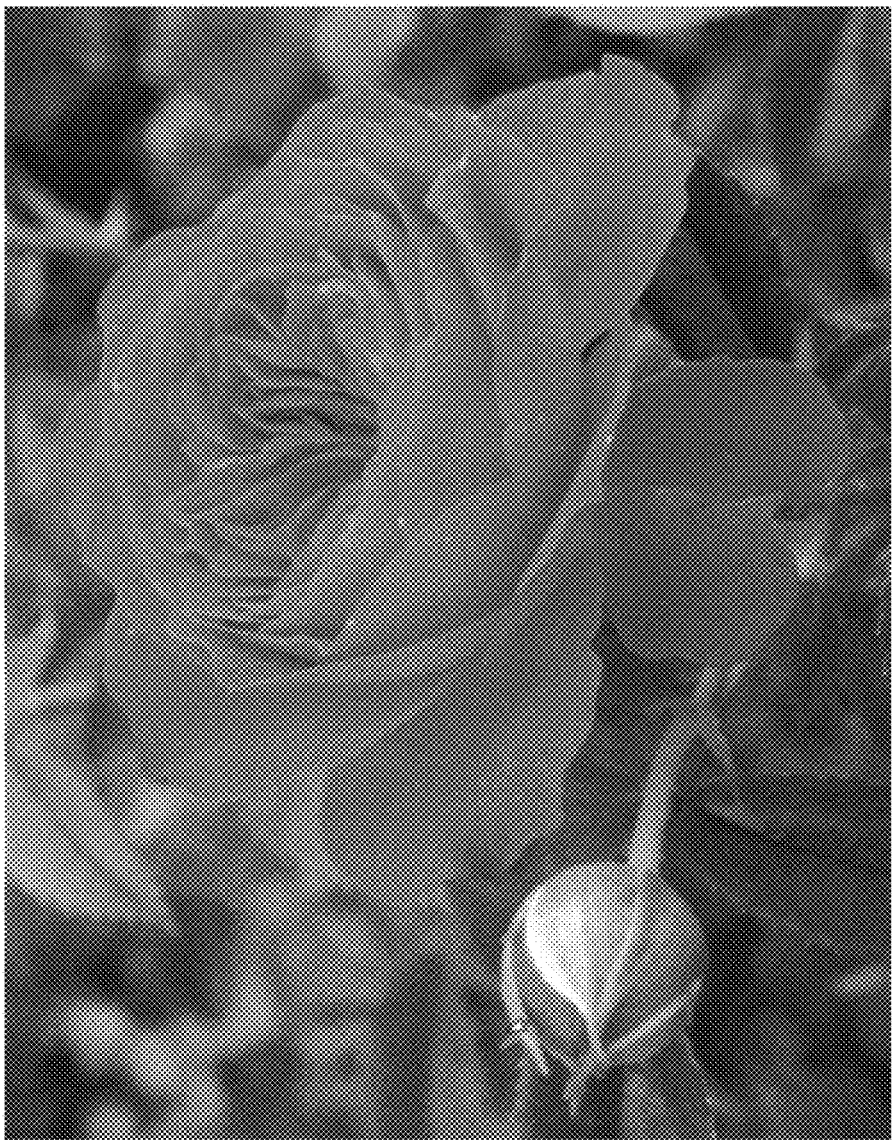

* * * * *